United States Patent
Watanabe et al.

(10) Patent No.: US 12,285,449 B2
(45) Date of Patent: Apr. 29, 2025

(54) FERMENTED MILK FOR IMPROVING AUTONOMIC NERVOUS FUNCTION

(71) Applicants: MEIJI CO., LTD., Tokyo (JP); University Public Corporation Osaka, Osaka (JP)

(72) Inventors: Yasuyoshi Watanabe, Osaka (JP); Kei Mizuno, Osaka (JP); Jun Henmi, Tokyo (JP); Seiya Makino, Tokyo (JP); Hiroshi Kano, Tokyo (JP)

(73) Assignees: MEIJI CO., LTD, Tokyo (JP); UNIVERSITY PUBLIC CORPORATION OSAKA, Osaka (JP)

( * ) Notice: Subject to any disclaimer, the term of this patent is extended or adjusted under 35 U.S.C. 154(b) by 0 days.

(21) Appl. No.: 17/828,772

(22) Filed: May 31, 2022

(65) Prior Publication Data

US 2022/0288140 A1    Sep. 15, 2022

Related U.S. Application Data

(63) Continuation of application No. 16/864,486, filed on May 1, 2020, now abandoned.

(30) Foreign Application Priority Data

May 13, 2019  (JP) .................... 2019-090381

(51) Int. Cl.
   *A61K 35/747*   (2015.01)
   *A61K 35/20*    (2006.01)
   *A61P 25/28*    (2006.01)

(52) U.S. Cl.
   CPC ............ *A61K 35/747* (2013.01); *A61K 35/20* (2013.01); *A61P 25/28* (2018.01)

(58) Field of Classification Search
   None
   See application file for complete search history.

(56) References Cited

U.S. PATENT DOCUMENTS

2010/0150891 A1* 6/2010 Beppu ............... A61P 25/02
                                                                    435/146
2012/0009163 A1  1/2012 Sawada et al.

FOREIGN PATENT DOCUMENTS

| CN | 103221531 | 7/2013 | |
|---|---|---|---|
| CN | 108495558 | 9/2018 | |
| JP | 2011-116666 | 6/2011 | |
| JP | 2011-126833 | 6/2011 | |
| JP | 5177728 | 4/2013 | |
| JP | 2015-96542 | 5/2015 | |
| JP | 2018-184361 | 11/2018 | |
| WO | 2015/133122 | 9/2015 | |
| WO | WO-2017083470 A1 * | 5/2017 | ............ A61K 35/74 |
| WO | 2018/225556 | 12/2018 | |

OTHER PUBLICATIONS

Otomi et al. Health, 7, 397-405, 2015.*
Makino et al. Nutrients 2018, 10, 798, Jun. 21, 2018.*
Seiya Makino et al., "Anti-Fatigue Effects of Yogurt Fermented with Lactobacillus delbrueckii subsp. bulgaricus OLL1073R-1 in healthy People Suffering from Summer Heat Fatigue: A Randomized, Double-Blind, Placebo-Controlled Trail", Nutrients, vol. 10, No. 798, pp. 1-10, 2018.
Kaiho Otomi et al., "Effects of Yogurt Containing Lactobacillus gasseri OLL2716 on Autonomic Nerve Activities and Physiological Functions", Health, vol. 7, pp. 397-405, 2015.

* cited by examiner

*Primary Examiner* — Oluwatosin A Ogunbiyi
(74) *Attorney, Agent, or Firm* — Wenderoth, Lind & Ponack, L.L.P.

(57) ABSTRACT

A fermented milk for improving autonomic nervous function containing at least one lactic acid bacterial species of the genus *Lactobacillus* and its metabolite. The lactic acid bacterial species of the genus *Lactobacillus* is selected from the group consisting of *Lactobacillus delbrueckii*, *Lactobacillus delbrueckii* subsp. *bulgaricus*, *Lactobacillus gasseri*, *Lactobacillus rhamnosus* and *Lactobacillus acidophilus*. The lactic acid bacterial strain of the genus *Lactobacillus* is preferably *Lactobacillus delbrueckii* subsp. *bulgaricus* OLL1073R-1(FERM BP-10741).

8 Claims, 1 Drawing Sheet

[Figure 1]
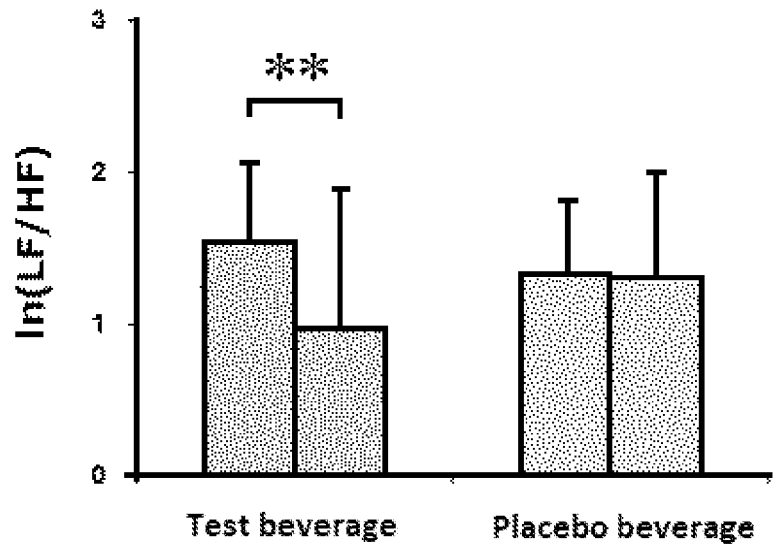
[Figure 2]
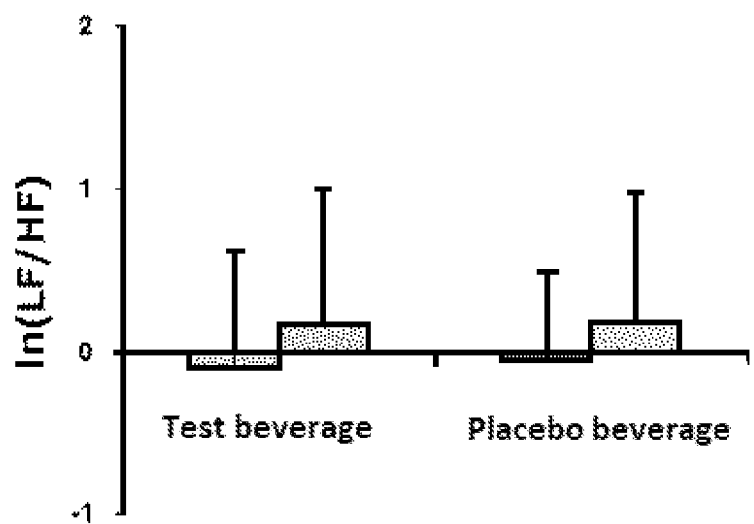

FERMENTED MILK FOR IMPROVING AUTONOMIC NERVOUS FUNCTION

CROSS-REFERENCE TO RELATED APPLICATION

This application is a continuation of U.S. application Ser. No. 16/864,486, filed on May 1, 2020, now abandoned, which claims the benefit of priority of Japanese Patent Application No. 2019-090381, filed on May 13, 2019, the entire contents of which are incorporated herein by reference.

TECHNICAL FIELD

The present invention relates to fermented milk for improving autonomic nervous function.

BACKGROUND ART

Autonomic nervous system is composed of sympathetic nerves and parasympathetic nerves. If one of them is disturbed and the balance is broken, cold, stiffness, gastrointestinal disorder and the like occur, which adversely affects daily life. When humans are stressed, adrenocortical hormones are secreted from adrenal cortex and adrenaline and the like are secreted from adrenal medulla in the adrenal cortex, which is innervated by the sympathetic nerves, by order from brain. These hormones have a variety of effects, including elevated blood glucose, elevated blood pressure, immunosuppression, gastric acid secretion stimulation, arousal and the like. For this reason, if the sympathetic nerve continues to become dominant due to the stress of a person, the person is liable to suffer from a problem such as poor physical condition. The precautions and countermeasures for that include calcium intake and moderate exercise. In recent years, there has been a need for easy-to-use measures such as consuming foods that are effective in improving autonomic nervous function.

Several foods and compositions for improving autonomic nervous function have been investigated. For example, Japanese Patent Application Laid-Open No. 2018-184361 (Patent Document 1) discloses a composition for autonomous neural adjustment that contains diketopiperazines or the salt as an active component.

PRIOR ART LITERATURE

Patent Document

[PATENT DOCUMENT 1] Japanese Patent Application Laid-Open No. 2018-184361

SUMMARY OF THE INVENTION

Problem to be Solved by the Invention

However, there is still no food that can be used in a normal diet and has an improving effect on the autonomic nervous function. Therefore, an objective of the present invention is to provide a food product for improving the autonomic nervous function which can be easily and familiarly ingested.

Means for Solving the Problems

In order to solve the above-mentioned problems, the present inventors focused on fermented milk as a food that can be easily and familiarly ingested, and examined in detail the effect of the fermented milk on improving autonomic nervous function. As a result, it has been found that ingestion of fermented milk prepared using a specific lactic acid bacteria of the genus *Lactobacillus* and its metabolites had significantly reduction of the relative sympathetic nerve activity index, resulting in improvement of autonomic nervous function on humans having a relative sympathetic nerve activity index (=(low frequency component (LF) of 0.04 Hz to 0.15 Hz reflecting sympathetic nerve function)/(high frequency component (HF) of 0.15 Hz to 0.40 Hz mainly reflecting parasympathetic nerve function)) of 2.0 or more to ingest fermented milk containing lactic acid bacteria, and the present invention has been completed.

That is, the present invention is as follows.

(1) A fermented milk for improving autonomic nervous function containing at least one species of lactic acid bacteria of the genus *Lactobacillus* and its metabolite, wherein the species of lactic acid bacteria of the genus *Lactobacillus* is selected from the group consisting of *Lactobacillus delbrueckii*, *Lactobacillus delbrueckii* subsp. *bulgaricus*, *Lactobacillus gasseri*, *Lactobacillus rhamnosus* and *Lactobacillus acidophilus*.

Here, "improvement of autonomic nervous function" means that the relative sympathetic nerve activity index is significantly decreased. That is to say, the present invention can be translated as "A fermented milk for reduction of relative sympathetic nerve activity index containing lactic acid bacteria of the genus *Lactobacillus* selected from the group consisting of *Lactobacillus delbrueckii*, *Lactobacillus delbrueckii* subsp. *bulgaricus*, *Lactobacillus gasseri*, *Lactobacillus rhamnosus* and *Lactobacillus acidophilus*, and its metabolite.

(2) The fermented milk according to (1) or (1), the lactic acid bacterial species of the genus *Lactobacillus* is *Lactobacillus delbrueckii* subsp. *bulgaricus* OLL1073R-1(FERM BP-10741).

The present invention also includes the following inventions.

(3) A method for improving autonomic nervous function, feeding a subject with a fermented milk containing at least one lactic acid bacterial species of the genus *Lactobacillus* and its metabolite, wherein the genus *Lactobacillus* is selected from the group consisting of *Lactobacillus delbrueckii*, *Lactobacillus delbrueckii* subsp. *bulgaricus*, *Lactobacillus gasseri*, *Lactobacillus rhamnosus* and *Lactobacillus acidophilus*.

(4) The method according to (3), wherein the lactic acid bacterial strain is *Lactobacillus delbrueckii* subsp. *bulgaricus* OLL1073R-1(FERM BP-10741).

(5) Use of at least one lactic acid bacterial species of the genus *Lactobacillus* in production of fermented milk for improving autonomic nervous function, wherein the lactic acid bacterial species of the genus *Lactobacillus* is selected from the group consisting of *Lactobacillus delbrueckii*, *Lactobacillus delbrueckii* subsp. *bulgaricus*, *Lactobacillus gasseri*, *Lactobacillus rhamnosus* and *Lactobacillus acidophilus*.

(6) The use according to (5), wherein the lactic acid bacterial strain is *Lactobacillus delbrueckii* subsp. *bulgaricus* OLL1073R-1(FERM BP-10741).

(7) At least one lactic acid bacterial species of the genus *Lactobacillus* selected from the group consisting of *Lactobacillus delbrueckii*, *Lactobacillus delbrueckii* subsp. *bulgaricus*, *Lactobacillus gasseri*, *Lactobacillus* rhamnosus and *Lactobacillus acidophilus*, for use in production of fermented milk for improving autonomic nervous function.

(8) *Lactobacillus delbrueckii* subsp. *bulgaricus* OLL1073R-1(FERM BP-10741) for use in production of fermented milk for improving autonomic nervous function.

(9) A composition for improving autonomic nervous function containing at least one lactic acid bacterial species of the genus *Lactobacillus* and its metabolite as an active ingredient, wherein the lactic acid bacterial species of the genus *Lactobacillus* is selected from the group consisting of *Lactobacillus delbrueckii, Lactobacillus delbrueckii* subsp. *bulgaricus, Lactobacillus gasseri, Lactobacillus rhamnosus* and *Lactobacillus acidophilus* (Note that the term "metabolite" as used herein means a substance produced as a result of fermentation of milk by lactic acid bacteria; the term "metabolite" includes the above-mentioned fermented milk.).

(10) A method of using at least one lactic acid bacterial species of the genus *Lactobacillus* and its metabolite as an autonomic nervous function improving agent, wherein the lactic acid bacterial species of the genus *Lactobacillus* is selected from the group consisting of *Lactobacillus delbrueckii, Lactobacillus delbrueckii* subsp. *bulgaricus, Lactobacillus gasseri, Lactobacillus rhamnosus* and *Lactobacillus acidophilus*.

(11) A method of improving autonomic nervous function by administering at least one lactic acid bacterial species of the genus *Lactobacillus* and its metabolite, wherein the lactic acid bacterial species of the genus *Lactobacillus* is selected from the group consisting of *Lactobacillus delbrueckii, Lactobacillus delbrueckii* subsp. *bulgaricus, Lactobacillus gasseri, Lactobacillus rhamnosus* and *Lactobacillus acidophilus*.

(12) A metabolite of lactic acid bacterial species of the genus *Lactobacillus* selected from the group consisting of *Lactobacillus delbrueckii, Lactobacillus delbrueckii* subsp. *bulgaricus, Lactobacillus gasseri, Lactobacillus rhamnosus* and *Lactobacillus acidophilus* for use as an autonomic nervous function improving agent.

(13) At least one lactic acid bacterial species of the genus *Lactobacillus* selected from the group consisting of *Lactobacillus delbrueckii, Lactobacillus delbrueckii* subsp. *bulgaricus, Lactobacillus gasseri, Lactobacillus rhamnosus* and *Lactobacillus acidophilus* for use as an autonomic nervous function improving agent.

(14) Use of a metabolite of one lactic acid bacterial species of the genus *Lactobacillus* selected from the group consisting of *Lactobacillus delbrueckii, Lactobacillus delbrueckii* subsp. *bulgaricus, Lactobacillus gasseri, Lactobacillus rhamnosus* and *Lactobacillus acidophilus* in production of a composition for improving autonomic nervous function.

(15) Use of at least one lactic acid bacterial species of the genus *Lactobacillus* selected from the group consisting of *Lactobacillus delbrueckii, Lactobacillus delbrueckii* subsp. *bulgaricus, Lactobacillus gasseri, Lactobacillus rhamnosus* and *Lactobacillus acidophilus* in production of fermented milk for improving autonomic nervous function.

(16) A method for producing a composition for improving autonomic nervous function by supplying a milk raw material to at least one lactic acid bacterial species of the genus *Lactobacillus* selected from the group consisting of *Lactobacillus delbrueckii, Lactobacillus del-* *brueckii* subsp. *bulgaricus, Lactobacillus gasseri, Lactobacillus rhamnosus* and *Lactobacillus acidophilus.*

Effect of the Invention

According to the present invention, the autonomic nervous function can be remarkably improved by ingesting fermented milk prepared with at least one lactic acid bacterial species of the genus *Lactobacillus* selected from the group consisting of *Lactobacillus delbrueckii, Lactobacillus delbrueckii* subsp. *bulgaricus, Lactobacillus gasseri, Lactobacillus rhamnosus* and *Lactobacillus acidophilus*. In particular, fermented milk is a food with extensive dietary experience and can be easily and familiarly ingested. Therefore, it is an effective countermeasure against various symptoms caused by disturbance of autonomic nervous system, and can greatly contribute to improvement of the autonomic nervous function.

BRIEF DESCRIPTION OF THE DRAWINGS

FIG. 1 is a graph showing the relative sympathetic nerve activity index of subjects before the consumption of the test beverage and placebo beverage to the subjects in the high sympathetic activity group, respectively, in conjunction with the relative sympathetic nerve activity index of the subjects after 4 weeks of consumption of the beverages, in Study Example 1. ** mark indicates significant differences in the unpaired t-test at a risk of less than 1%.

FIG. 2 is a graph showing the relative sympathetic nerve activity index of the subjects before the consumption of the test beverage and placebo beverage to the subjects in the low sympathetic activity group, respectively, in conjunction with the relative sympathetic nerve activity index of the subjects after 4 weeks of consumption of the beverages, in Study Example 2.

MODE FOR CARRYING OUT THE INVENTION

In the present invention, a fermented milk is prepared using at least one least one lactic acid bacterial species of the genus *Lactobacillus* selected from the group consisting of *Lactobacillus delbrueckii, Lactobacillus delbrueckii* subsp. *bulgaricus, Lactobacillus gasseri, Lactobacillus rhamnosus* and *Lactobacillus acidophilus*. As a method of preparing the fermented milk, for example, "a method of adding a lactic acid bacterium starter containing the above-mentioned lactic acid bacteria of the genus *Lactobacillus* to raw milk after the raw milk is sterilized and cooled, and fermenting the raw milk containing the lactic acid bacterium starter at a fermentation temperature and a fermentation time such that the fermented milk has a predetermined lactic acid acidity". Examples of the lactic acid acidity include 0.6 to 1.2 mass %. Examples of the fermentation temperature include 40 to 45° C. Examples of the fermentation time include 2 to 12 hours.

The term "lactic acid bacteria" in the present invention is a generic term for all bacteria classified as lactic acid bacteria, and is not limited by bacterial species, strains, and the like. It should be noted that the lactic acid bacteria may be classified into either plant origin or animal origin depending on their origin. In the present invention, any of the lactic acid bacteria derived from plants and the lactic acid bacteria derived from animals can be used. As the strain of the lactic acid bacteria of the present invention, one or more strains selected from lactic acid bacterial species of the genus *Lactobacillus* are preferable because they have sufficient eating experience with fermented milk such as yoghurt. The lactic acid bacteria of the genus *Lactobacillus* is preferably at least one lactic acid bacterial species of the genus *Lactobacillus delbrueckii, Lactobacillus delbrueckii* subsp. *bulgaricus, Lactobacillus gasseri, Lactobacillus rhamnosus*, and *Lactobacillus acidophilus*, more preferably *Lactobacillus delbrueckii* subsp. *bulgaricus*, and more preferably "*Lactobacillus delbrueckii* subsp. *bulgaricus* OLL1073R-1) (deposit number: FERM BP-10741)".

In addition, as the lactic acid bacterium starter, it is preferable to use *thermophilus* bacteria or *Streptococcus thermophilus* in combination with lactic acid bacteria of the genus *Lactobacillus* from the viewpoint of productivity and palatability. Further, when the lactic acid bacterial species of the genus *Lactobacillus* is *Lactobacillus delbrueckii* subsp. *bulgaricus* OLL1073R-1 (deposit number: FERM BP-10741), it is more preferable that the *thermophilus* bacterial strain is *Streptococcus thermophilus* 1131 or *Streptococcus thermophilus* OLS3059. Furthermore, lactic acid bacteria other than lactic acid bacterial species of the genus *Lactobacillus* and the *thermophilus* bacterial species and fermenting microorganisms such as *Bifidobacterium* and yeast may be added as a lactic acid bacterium starter or for the purpose of imparting functionality.

Herein, "*Lactobacillus delbrueckii* subsp. *bulgaricus* OLL1073R-1 has been deposited with the National Institute of Advanced Industrial Science and Technology under deposit number FERM BP-10741 (deposit date: Nov. 29, 2006). "*Streptococcus thermophilus* OLS3059" has been deposited with the National Institute of Advanced Industrial Science and Technology under deposit number FERM BP-10740 (deposit date: Nov. 29, 2006). *Streptococcus thermophilus* 1131 is available from Meiji Bulgaria Yoghurt "LB81" manufactured by Meiji Co., Ltd.

The term "fermented milk" in the present invention means a product obtained by fermenting milk, and includes, for example, but is not limited to "fermented milk", "lactic acid bacteria beverage", "milk beverage", "natural cheese" and the like defined in Ministerial Ordinance on Ingredient Standards for Milk and Dairy Products (Ministerial Ordinance on milk and the like). For example, fermented milk refers to "fermented milk" defined in Ministerial Ordinance on Ingredient Standards for Milk and Dairy Products; i.e., milk such as raw milk, cow milk, special milk, raw goat milk, sterilized goat milk, raw sheep milk, ingredient-adjusted milk, low-fat milk, fat-free milk, processed milk and the like, or milk containing an equivalent or higher fat-free milk solid content, fermented by lactic acid bacteria or yeast, made into a solid (hard type), gelatinous (soft type) or liquid (drink type), or frozen of these. In the fermented milk of the present invention, the range of concentration of the non-fat milk solid content is preferably, for example, 4.0% to 12.0%, more preferably 6.0% to 10.0%, and furthermore preferably 7.0% to 9.0%. The concentration of the milk fat content is preferably, for example, 0.2% to 4.0%, more preferably 0.3% to 3.0%, and furthermore preferably 0.4% to 2.0%.

Typical examples of fermented milk include yoghurt. The International Standard defined by Food and Agriculture Organization of the United Nations (FAO)/World Health Organization (WHO) also stipulates that "products called yoghurts are produced from dairy products such as milk and fat-free dry milk by the lactic acid fermentative action of both *Streptococcus thermophilus, Lactobacillus delbrueckii* ssp. *bulgaricus*, and that the two aforementioned bacteria are abundantly viable in the final products." In the present invention, "yoghurt" is intended to include yoghurt as defined in the above-mentioned FAO/WHO. The yoghurts include, for example, plain yoghurt, hard yoghurt (set type yoghurt), soft yoghurt, drink yoghurt, and the like. In the present invention, a drink yoghurt is particularly preferable from the viewpoint of drinkability at the time of fatigue.

By forming the fermented milk of the present invention in the form of a single package in an amount suitable for single ingestion, the fermented milk of the present invention can be ingested appropriately and easily, which is preferable from the viewpoint of usability. The amount appropriate for a single ingestion, although there are individual differences and variations depending on the degree of fatigue to be improved or the like, for example, in the case of fermented milk having a Non-fat milk solids of 8.0%, it is preferably in the range of 50 mL to 200 mL per dose, more preferably in the range of 80 mL to 150 mL per dose, and more preferably in the range of 100 mL to 120 mL per dose. Alternatively, it is preferably in the range of 50 g to 200 g per dose, more preferably in the range of 80 g to 150 g per dose, and furthermore preferably in the range of 100 g to 120 g per dose.

In the present invention, "the form of a single package" encompasses all forms, e.g. common packaging forms, such as a lidded container, capped bottle, individual bag, pouch, tube, and the like. In the present invention, the use of the fermented milk can be clarified by describing the use, efficacy, ingestion method, and the like of the fermented milk according to the invention in each individual package or a package including a plurality of individual packages, and/or by enclosing the substance and the like which describe the description, and/or by posting a separate pamphlet and the like which describe the description, and the like.

From the viewpoint of enhancing the improvement effect of the autonomic nervous function, the fermented milk of the present invention is preferably ingested continuously for 4 weeks or longer, more preferably for 6 weeks or longer, furthermore preferably for 8 weeks or longer, furthermore preferably for 10 weeks or longer, furthermore preferably for 12 weeks or longer, furthermore preferably for 24 weeks or longer, and particularly preferably for 36 weeks or longer. Since the fermented milk of the present invention has sufficient dietary experience and can be safely ingested, the upper limit of the ingestion period is not particularly limited and can be permanently continued, but if the upper limit is forcibly set, it is, for example, 60 weeks or less. The upper limit may be, for example, 120 weeks or less, 100 weeks or less, or 80 weeks or less depending on the degree of feeling of fatigue to be improved and the individual difference.

The fermented milk of the present invention can be ingested to improve autonomic nervous function. Specifically, it is expected that it can improve "cold", "stiffness", "gastrointestinal disorder", "exacerbation of depression", "exacerbation of dizziness", "increase of heart rate", "increase of blood pressure" and "exacerbation of chronic pain". That is, according to the present invention, it is possible to expect improvement of "cold", "stiffness", "gastrointestinal disorder", "exacerbation of depression", "exacerbation of dizziness", "increase of heart rate", "increase of blood pressure", "exacerbation of chronic pain" and the like by fermented milk which can be easily and familiarly ingested. Here, whether the lactic acid bacteria in the fermented milk is live bacteria or dead bacteria, the fermented milk can exhibit the same improving effect.

Incidentally, it is preferable to label an explanation of the use, the efficacy, the function, the type of the active ingredient, the method of use, and the like of the fermented milk in the fermented milk of the present invention. "Labeling" as used herein includes all indications to inform consumers of the above effect. This labeling may be any indications capable of recalling or analogizing the labeling content described above, and may include any indications regardless of the purpose of the indications, the content of the indications, the object/medium to be indicated, or the like. For example, the description may be labeled on a package or container of a product, the description may be displayed or distributed on an advertisement or price list or transaction document related to the product, or the information containing the description may be provided by an electromagnetic (Internet or the like) method.

It is preferable that the product obtained by packaging the fermented milk for improving autonomic nervous function of the present invention is labeled, for example, "improvement of autonomic nervous function", "reduction of relative sympathetic nerve activity index", or the like.

Note that the words used for performing the above-mentioned indication are not limited to the above-described example, and may be words having the same meaning as the above-mentioned example. Such phrases may include, for example, various phrases for the consumer, such as "improve autonomic nervous function", "reduce relative sympathetic nerve activity index", "help improve autonomic nervous function," or "help reduce relative sympathetic nerve activity index".

The above-mentioned fermented milk may be in the form of a special use food, a comprehensive nutritional food, a nutritional supplement food, a specified health food, a functional label food, a processed food, or the like. In addition, the fermented milk may also be formulated in compositions such as beverages and liquid foods other than drink yoghurt.

In the present invention, the index of improvement in autonomic nervous function can be represented by a relative sympathetic nerve activity index. The relative sympathetic nerve activity index can be determined by dividing the "low frequency component (LF) of 0.04 Hz to 0.15 Hz that reflects sympathetic nerve function" by the high frequency component (HF) of 0.15 Hz to 0.40 Hz that primarily reflects parasympathetic nerve function.

The present invention has been found to have an effect of improving autonomic nervous function in fermented milk prepared using lactic acid bacterial species of the genus *Lactobacillus* by comparing a beverage containing lactic acid bacterial species of the genus *Lactobacillus* and a beverage not containing those *Lactobacillus* bacteria according to working examples described later. Thus, the present invention also provides lactic acid bacterial species of the genus *Lactobacillus* and its metabolite having an improving effect on autonomic nervous function. At this time, the ingestion of lactic acid bacterial species of the genus *Lactobacillus* per day for the purpose of obtaining the effect of improving the autonomic nervous function varies depending on the age, sex, and the like, but can be appropriately determined by a person skilled in the art. These daily ingestions are preferably $10^6$ cfu or more, more preferably $10^7$ cfu or more, and more preferably $10^8$ cfu or more as lactic acid bacteria of the genus *Lactobacillus*. The upper limit of this ingestion is not particularly limited, for example, $10^{12}$ cfu.

The lactic acid bacteria of the present invention includes not only bacterial cell itself but also those derived from the bacterial cell such as a cell body crushed product. The metabolites of the lactic acid bacteria of the present invention include metabolite obtained by culturing or fermenting lactic acid bacteria. For example, *Lactobacillus delbrueckii* subsp. *bulgaricus* OLL1073R-1 (deposit number: FERM BP-10741), a lactic acid bacterial strain of the genus *Lactobacillus*, is known to produce extracellular polysaccharide (EPS) during its culturing, the use of this extracellular polysaccharide is also encompassed herein. In the present invention, the lower limit of the daily ingestion of this extracellular polysaccharide is 100 μg, preferably 500 μg, more preferably 1.0 mg, and furthermore preferably 2.0 mg. The upper limit is not particularly limited, but is, for example, 200 mg, preferably 100 mg, more preferably 70 mg, furthermore preferably 30 mg, and furthermore preferably 8.0 mg.

EXAMPLES

Hereinafter, the present invention will be described more specifically on the basis of working examples. These working examples do not limit the present invention.

Preparation Example 1

Mixture A containing raw milk, non-fat dry milk, cream, liquid sugar, pectin, sugar, stevia and perfume was fermented by adding *Lactobacillus delbrueckii* subsp. *bulgaricus* OLL1073R-1 (deposit number: FERM BP-10741) and *Streptococcus thermophilus* 1131 as a starter to prepare a drink-type yoghurt (hereinafter referred to as a "test beverage") having a fat-free milk solids of 8.1% and a milk fat content of 0.5%. 112 mL of the test beverage was immediately filled into each of containers (plain capped PET bottles without a mark and the like.) after preparation. The nutrients of the test beverages were 76 kcal energy amount, 3.6 g protein, 0.67 g lipid, 13.9 g carbohydrate and 13.3 g sugars per one container (112 ml).

Preparation Example 2

Mixture B containing cow milk, non-fat dry milk, milk protein, liquid sugar, pectin, sugar, stevia, lactic acid and perfume was sterilized to prepare a beverage (hereinafter referred to as a "placebo beverage"). 112 mL of the placebo beverage was immediately filled into each of containers which are same as the containers filled with the test beverage after preparation. The general composition (non-fat milk solids, fat), nutrients (proteins, lipid, carbohydrate, sugar) and energy amount of this placebo beverage are equivalent to those of the test beverage of Preparation Example 1, but lactic acid bacteria are not included in this placebo beverage.

Test Example 1

A randomized placebo-controlled double-blind crossover comparative study was conducted in 53 healthy men and women aged 30-60 years from among those volunteered at Osaka City University's Center for Health Sciences and Innovation (excluding those with autonomic nervous system disorders (LF/HF>=10) when the 53 subjects were selected). The details are described as follows;

First, the 53 subjects were divided into 27 subjects (hereinafter referred to as "group A") and 26 subjects (hereinafter referred to as "group B"), and the relative sympathetic nerve activity index (LF/HF) at rest and with their eyes closed was determined. Thereafter, the subjects in the group A were allowed to drink two test beverages daily at any time for 4 weeks, and the subjects in the group B were allowed to drink two placebo beverages daily, then their relative sympathetic nerve activity index (LF/HF) at rest and with their eyes closed was determined. The subject's relative sympathetic nerve activity index (LF/HF) at rest and closing of the eyes of the subjects was then determined 3 weeks (the washout period (period during which the test drink was not consumed)) after. Thereafter, the subjects in the group B were allowed to drink two test beverages daily for 4 weeks, and the subjects in the group A were allowed to drink two placebo beverages daily for 4 weeks, then their relative sympathetic nerve activity index (LF/HF) at rest and with their eyes closed was determined.

In addition, regardless of the groups A and B, the relative sympathetic nerve activity index (LF/HF) of each subject was derived prior to the start of the above-mentioned study, and the group of subjects whose relative sympathetic nerve activity index was 2.0 or more (ln(LF/HF) is 0.693 or more) was set as the high sympathetic nerve activity group, and the group of subjects whose relative sympathetic nerve activity index was less than 2.0 (ln(LF/HF) is less than 0.693) was set as the low sympathetic nerve activity group. The cut-off value in this placebo-controlled double-blind crossover comparative study was established with reference to the following fatigue-degree assessment criteria using LF/HF disclosed in References 1 and 2.

According to Reference 1, the activity balancing LF/HF of the sympathetic nervous system and the parasympathetic nervous system of the normal person lying on his back was 1.5 to 2.0. According to Reference 2, a person with a LF/HF of 2.0 to 5.0 has a slight disruption in the activity balance of the sympathetic nervous system and the parasympathetic nervous system and the person is in the sympathetic nervous-dominant state, and a person with a LF/HF of 5.0 or more has a large disruption in the activity balance of the sympathetic nervous system and the sympathetic nervous system and the person is in the sympathetic nervous-dominant state, which means that there is a risk of leading to a mental health disorder, and it is required to consult with a physician. Therefore, the cut-off value of the relative sympathetic nerve activity index was set to 2.0 here.

Reference 1: Task Force of the European Society of Cardiology and the North American Society of Pacing and Electrophysiology. Heart rate variability. Standards of measurement, physiological interpretation, and clinical use. Eur. Heart J., 7(3): 354-381 (1996)

Reference 2: Japanese Patent No. 5491749 specification

The relative sympathetic nerve activity index was obtained by evaluating sympathetic nerve activity and parasympathetic nerve activity by pulse wave and electrocardiography (vital monitor: Fatigue Science Laboratory, Inc., measurement time: 3 minutes) of index fingers of both hands of subjects at rest and with their eyes closed and frequency analysis thereof. Specifically, the relative sympathetic nerve activity index is obtained by measuring low frequency component (LF) of 0.04 Hz to 0.15 Hz and high frequency component (HF) of 0.15 Hz to 0.40 Hz by frequency analysis of electrocardiogram R-R interval or acceleration pulse wave a-a interval of two-time differential waveform of or pulse wave and then dividing the low frequency component by the high frequency component.

The placebo-controlled double-blind crossover comparative study is shown in FIGS. 1 and 2. As is apparent from FIG. 1, the relative sympathetic nerve activity indices of the subjects in the high sympathetic nerve activity group who ingested the test beverage were significantly lower than those before ingestion of the test beverage. On the other hand, the relative sympathetic nerve activity indices of the subjects in the high sympathetic nerve activity group who ingested the placebo beverage were similar to those before the ingestion of the same test beverage. That is to say, it became clear that this test beverage effectively improved the autonomic nervous function of the subjects of the high sympathetic nerve activity group.

On the other hand, as is apparent from FIG. 2, when the subjects in the low sympathetic nerve activity group ingested the test beverage and the placebo beverage, their relative sympathetic nerve activity index did not decrease. That is, it was revealed that the test beverages did not affect their autonomic nervous function when the ingested subject was the subjects in the low sympathetic nerve activity group. In other words, it was revealed that the test beverage exerts its autonomic nervous improving function only on the subjects in the high sympathetic nerve activity group (that is, the people with unfavorable autonomic balance).

INDUSTRIAL APPLICABILITY

According to the present invention, it is possible to improve autonomic nervous function by the fermented milk which can be easily and familiarly ingested. Since fermented milk is a food with extensive dietary experience and can be easily and familiarly ingested, it is an effective countermeasure against various symptoms caused by disturbance of the autonomic nervous system, and can greatly contribute to improvement of the autonomic nervous function, and is very useful.

Accession No

FERM BP-10741
FERM BP-10740

The invention claimed is:

1. A method of reducing a relative sympathetic nerve activity index comprising:
    administering 80 g/dose to 150 g/dose or 80 mL/dose to 150 mL/dose of a fermented milk comprising *Lactobacillus delbrueckii* subsp. *bulgaricus* and its metabolite, and 7.0% to 9.0% of non-fat milk solid content, twice per day for 4 weeks or longer, to a subject in need thereof,
    wherein the method is effective for reducing the relative sympathetic nerve activity index beginning at least 4 weeks from the administration of the fermented milk.

2. The method according to claim 1,
    wherein the *Lactobacillus delbrueckii* subsp. *bulgaricus* is *Lactobacillus delbrueckii* subsp. *bulgaricus* OLL1073R-1 (FERM BP-10741).

3. The method according to claim 1,
    wherein the metabolite is an extracellular polysaccharide of the lactic acid bacteria.

4. The method according to claim 1,
    wherein administering 100 mL/dose to 120 mL/dose or 100 g/dose to 120 g/dose of a fermented milk containing at least one lactic acid bacterial species of the genus *Lactobacillus delbrueckii* subsp. *bulgaricus* and its metabolite, and 7.0% to 9.0% of non-fat milk solid content, twice per day for 4 weeks or longer, to a subject in need thereof.

5. The method according to claim 1,
    wherein administering 110 mL/dose to 120 mL/dose or 110 g/dose to 120 g/dose of a fermented milk containing at least one lactic acid bacterial species of the genus *Lactobacillus delbrueckii* subsp. *bulgaricus* and its metabolite, and 7.0% to 9.0% of non-fat milk solid content, twice per day for 4 weeks or longer, to a subject in need thereof.

6. The method according to claim 1, the subject is the subject whose relative sympathetic nerve activity index is 2.0 or more.

7. The method according to claim 1, wherein the fermented milk further comprises a *thermophilus* bacterial strain.

8. The method according to claim 7, wherein the *thermophilus* bacterial strain is *Streptococcus thermophilus* OLS3059 (FERM BP-10740).

\* \* \* \* \*